(12) United States Patent
Kelly et al.

(10) Patent No.: US 6,995,157 B2
(45) Date of Patent: Feb. 7, 2006

(54) SUBSTITUTED 4,5-DIHYDRO-1,2,4-TRIAZIN-3-ONES, 1,2,4-TRIAZIN-3-ONES, AND THEIR USE AS FUNGICIDES AND INSECTICIDES

(75) Inventors: Martha Jean Kelly, Collegeville, PA (US); Richard Martin Jacobson, Chalfont, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 283 days.

(21) Appl. No.: 10/399,924

(22) PCT Filed: Oct. 26, 2001

(86) PCT No.: PCT/US01/50162

§ 371 (c)(1), (2), (4) Date: Apr. 24, 2003

(87) PCT Pub. No.: WO02/056682

PCT Pub. Date: Jul. 25, 2002

(65) Prior Publication Data

US 2004/0019209 A1    Jan. 29, 2004

Related U.S. Application Data

(60) Provisional application No. 60/243,801, filed on Oct. 27, 2000.

(51) Int. Cl.
*A61K 31/53* (2006.01)
*A01N 43/707* (2006.01)
*C07D 253/06* (2006.01)

(52) U.S. Cl. .................................. 514/242; 544/182
(58) Field of Classification Search ............... 544/182; 514/242

See application file for complete search history.

(56) References Cited

U.S. PATENT DOCUMENTS 5,994,355 A * 11/1999 Miki et al. .................. 514/242
6,159,980 A    12/2000 Arvanitis et al. ........... 514/255
6,825,192 B1  11/2004 Ito et al. ................... 514/222.5

FOREIGN PATENT DOCUMENTS

DE           42 39 540 A1    5/1994

* cited by examiner

*Primary Examiner*—Venkataraman Balasubramanian
(74) *Attorney, Agent, or Firm*—Lynn M. Zettler; Carl Corvin

(57) ABSTRACT

This invention relates to dihydrotriazinones, triazinones and related compounds, compositions comprising such compounds and an agronomically acceptable carrier, and the use thereof as broad spectrum fungicides and insecticides. This invention also teaches methods of preparing these compounds as well as methods of using the compounds as fungicides and insecticides.

6 Claims, No Drawings

SUBSTITUTED 4,5-DIHYDRO-1,2,4-TRIAZIN-3-ONES, 1,2,4-TRIAZIN-3-ONES, AND THEIR USE AS FUNGICIDES AND INSECTICIDES

This application is a 371 of PCT/US01/50162 filed 26 Oct. 2001, which claims benefit of U.S. Provisional Application No. 60/243,801 filed 27 Oct. 2000.

The need continues for novel and improved broad spectrum, agrochemical fungicides and insecticides. This is particularly so since the targets of fungicides and insecticides can become resistant to known fungicides and insecticides over time and after use of such compounds and their compositions. Additionally, economic and environmental considerations can favor fungicides and insecticides having different modes of performance than those currently used. This invention relates to dihydrotriazinones, triazinones and related compounds, compositions comprising such compounds and an agronomically acceptable carrier, and the use thereof as broad spectrum fungicides and insecticides. This invention also teaches methods of preparing these compounds as well as methods of using the compounds as fungicides and insecticides.

Some triazinones, among other nitrogen containing heterocycles, are disclosed by Kanellakopulos et al. in U.S. Pat. No. 5,814,645, Sep. 29, 1998 as having insecticidal activity, but the compounds of the present invention are not disclosed. Furthermore, some triazinones, among other nitrogen containing heterocycles, are disclosed by Michelotti et al. in U.S. Pat. No. 5,552,409, Sep. 3, 1996 as having fungicidal activity, but the compounds of the present invention are not disclosed.

One embodiment of this invention relates to a compound of the formula (I)

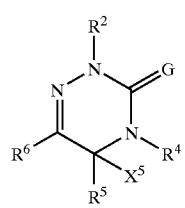

(I)

wherein $R^2$ is alkyl, haloalkyl, cyano, alkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl, phenylthioalkyl, or phenalkyl or phenylthioalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, or furyl or thienyl substituted with halo or alkyl on the furyl or thienyl ring, benzothienyl, benzofuranyl or benzothienyl or benzofuranyl substituted with halo, alkyl or haloalkyl, $R^4$ is a hydrogen atom, alkyl, haloalkyl, cycloalkyl, cycloalkylalkyl, alkylsulfonyl, cyano, alkynyl, haloalkynyl, haloalkoxycarbonyl, alkoxycarbonylthio, (alkylthio) carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl, aryloxythiocarbonyl, arylthiothiocarbonyl arylsulfonyl, or aryloxythiocarbonyl, arylthiothiocarbonyl, arylsulfonyl, substituted on an aromatic ring with from one to two substituents independently selected from halo and alkyl, $R^5$ is a hydrogen atom, alkoxy, alkylthio, hydroxy, mercapto, cyano, amino, alkylamino, dialkylamino wherein the alkyl groups may be the same or different or together with the nitrogen to which they are attached form a 5- or 6-membered heterocyclic ring, alkylcarbonyloxy, alkylcarbonylthio, alkoxycarbonyloxy, alkoxycarbonylthio, phenylcarbonyloxy, phenylcarbonylthio, phenylthio, phenoxy or phenylcarbonyloxy, phenylcarbonylthio, phenylthio, phenoxy, substituted on the phenyl ring with from one to three substituents independently selected from the group consisting of alkyl, halo, alkoxy, haloalkyl, haloalkoxy, $R^6$ is aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, thienyl, quinolinyl, isoquinolinyl, benzofuranyl, benzothienyl, pyridyl, pyridazinyl, pyrimidinyl, and furyl, thienyl, pyridyl, pyridazinyl, pyrimidinyl, substituted with one or two substituents independently selected from halo, alkyl, alkoxy, haloalkoxy, haloalkyl, alkylthio, haloalkylthio, nitro and cyano, $X^5$ is a hydrogen atom, G is an oxygen atom, a sulfur atom, or the agronomically acceptable salts, isomers, tautomers, enantiomers and mixtures thereof, provided that:

when $R^2$ is a phenalkyl, thenyl or substituted phenalkyl or thenyl and $X^5$ is a hydrogen atom, $R^4$ is not cyano, alkylsulfonyl or polyhaloalkyl, and when $R^2$ is methyl, phenyl, 2-methylphenyl, 4-methoxyphenyl or benzyl, $R^6$ is not phenyl or 4-bromophenyl.

The term "alkyl" includes both branched and straight chain alkyl groups. Typical alkyl groups are methyl, ethyl, n-propyl, isopropyl, n-butyl, sec-butyl, isobutyl, tert-butyl, pentyl, isopentyl, n-hexyl, n-heptyl, isooctyl, nonyl, decyl, undecyl, dodecyl and the like.

The term "halo" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, 2,2,2-trifluoroethyl, perfluoropropyl, 8-chlorononyl and the like.

The term "cyanoalkyl" refers to an alkyl group substituted with a cyano group, for example cyanomethyl, 2-cyanoethyl and the like.

The term "alkoxy" includes both branched and straight chain alkyl groups attached to a terminal oxygen atom. Typical alkoxy groups include methoxy, ethoxy, n-propoxy, isopropoxy, tert-butoxy and the like.

The term "alkoxyalkyl" refers to an alkyl group substituted with an alkoxy group, for example isopropoxymethyl.

The term "haloalkoxy" refers to an alkoxy group substituted with one or more halo groups, for example chloromethoxy, trifluoromethoxy, difluoromethoxy, perfluoroisobutoxy and the like.

The term "haloalkoxycarbonyl" refers to an alkoxy group substituted with one or more halo groups attached to a carbonyl group, for example chloromethoxycarbonyl, trifluoromethoxycarbonyl, difluoromethoxycarbonyl, perfluoroisobutoxycarbonyl and the like.

The term "alkylthio" includes both branched and straight chain alkyl groups attached to a terminal sulfur atom, for example methylthio.

The term "haloalkylthio" refers to an alkylthio group substituted with one or more halo groups, for example trifluoromethylthio.

The term "arylthioalkyl" refers to a aryl group as defined hereinbefore substituted with an alkylthio group, for example phenylthiomethyl and the like.

The term "alkylsulfinyl" refers to a sulfinyl moiety substituted with an alkyl group, for example methylsulfinyl, n-propylsulfinyl and the like.

The term "alkylsulfonyl" refers to a sulfonyl moiety substituted with an alkyl group, for example mesyl, n-propylsulfonyl and the like.

The term "arylsulfonyl" refers to a sulfonyl moiety substituted with an aryl group, for example toluenesulfonyl and the like.

The term "alkylamino" refers to an alkyl group attached to a nitrogen atom, for example methylamino, isopropylamino and the like.

The term "dialkylamino" refers to two alkyl groups, which may be the same or different, attached to a nitrogen atom, for example dimethylamino, N-ethyl-N-methylamino and the like.

The term "trialkylsilylalkyl" refers to three alkyl groups, which may be the same or different, attached to a silicon atom which is in turn attached to an alkyl group, for example trimethylsilylmethyl.

The term "alkoxycarbonyl" refers to a straight chain or branched alkoxy attached to a carbonyl group, for example ethoxycarbonyl, methoxycarbonyl and the like.

The term "aryloxycarbonyl" refers to an aryloxy attached to a carbonyl group, for example phenoxycarbonyl and the like.

The term "alkoxyoxalyl" refers to a straight chain or branched alkoxy attached to a oxalyl group, for example ethoxyoxalyl, methoxyoxalyl and the like.

The term "alkylcarbonyloxyalkoxycarbonyl" refers to a straight chain or branched acyloxyalkoxycarbonyl, for example acetoxymethoxycarbonyl and the like.

The term "alkylcarbonyloxy" refers to a straight chain or branched alkyl attached to a carbonyl group which is in turn attached to a oxygen atom, for example acetoxy, tert-butylcarbonyloxy and the like.

The term "alkylcarbonylthio" refers to a straight chain or branched alkyl attached to a carbonyl group which is in turn attached to a sulfur atom, for example ethylcarbonylthio, methylcarbonylthio and the like.

The term "alkoxycarbonyloxy" refers to a straight chain or branched alkoxy attached to a carbonyl group which is in turn attached to a oxygen atom, for example ethoxycarbonyloxy, methoxycarbonyloxy and the like.

The term "alkoxycarbonylthio" refers to a straight chain or branched alkoxy attached to a carbonyl group which is in turn attached to a sulfur atom, for example ethoxycarbonylthio, methoxycarbonylthio and the like.

The term "arylcarbonyloxy" refers to an unsubstituted or substituted phenyl attached to a carbonyl group which is in turn attached to a oxygen atom, for example benzoyloxy and the like.

The term "arylcarbonylthio" refers to an unsubstituted or substituted phenyl attached to a carbonyl group which is in turn attached to a sulfur atom, for example 4-chlorophenylcarbonylthio and the like.

The term "alkylcarbonyl" refers to an alkylketo functionality, for example acetyl, n-butyryl and the like.

The term "arylcarbonyl" refers to an arylketo functionality, for example benzoyl and the like.

The term "alkylcarbonylalkyl" refers to an alkylketoalkyl functionality, for example acetylmethyl and the like.

The term "cycloalkylcarbonyl" refers to an cycloalkylketo functionality, for example cyclopropylcarbonyl and the like.

The term "alkyl(thiocarbonyl)" refers to an alkyl functionality attached to a thiocarbonyl group, for example thioacetyl and the like.

The term "(alkylthio)carbonyl" refers to an alkylthio functionality attached to a carbonyl group, for example methylthiocarbonyl and the like.

The term "aryl(thiocarbonyl)" refers to an aryl functionality attached to a thiocarbonyl group, for example thiobenzoyl and the like.

The term "(arylthio)carbonyl" refers to an arylthio functionality attached to a carbonyl group, for example phenylthiocarbonyl and the like.

The term "alkylthiothiocarbonyl" refers to an alkylthio functionality attached to a thiocarbonyl group, for example propylthiothiocarbonyl and the like.

The term "alkenylthiothiocarbonyl" refers to an alkenylthio functionality attached to a thiocarbonyl group, for example allylthiothiocarbonyl and the like.

The term "alkynylthiothiocarbonyl" refers to an alkynylthio functionality attached to a thiocarbonyl group, for example propargylthiothiocarbonyl and the like.

The term "aryloxythiocarbonyl" refers to an aryloxy functionality attached to a thiocarbonyl group, for example phenoxythiocarbonyl and the like.

The term "arylthiothiocarbonyl" refers to an arylthio functionality attached to a thiocarbonyl group, for example phenylthiothiocarbonyl and the like.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, allenyl and the like.

The term "haloalkenyl" refers to an alkenyl group substituted with one or more halo groups.

The term "alkenyloxycarbonyl" refers to a straight chain or branched alkenyloxy attached to a carbonyl group, for example allyloxycarbonyl, vinyloxycarbonyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkynyloxycarbonyl" refers to a straight chain or branched alkynyloxy attached to a carbonyl group, for example propargyloxycarbonyl and the like.

The term "cycloalkyl" refers to a cyclic aliphatic ring structure, optionally substituted with alkyl, hydroxy and halo, such as cyclopropyl, methylcyclopropyl, cyclobutyl, 2-hydroxycyclopentyl, cyclohexyl, 4-chlorocyclohexyl, cycloheptyl, cyclooctyl and the like.

The term "cycloalkylalkyl" refers to a cycloalkyl group as defined hereinbefore attached to an alkyl group, for example cyclopropylmethyl, cyclohexylethyl and the like.

The term "cycloalkylalkynyl" refers to a cycloalkyl group as defined hereinbefore attached to an alkynyl group, for example cyclopropylpropargyl, 4-cyclopentyl-2-butynyl and the like.

The term "aryl" refers to phenyl or naphthyl which may be optionally substituted. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, 4-(trifluoromethoxy)phenyl, naphthyl, 2-chloronaphthyl, 2,4-dimethoxyphenyl, 4-(trifluoromethyl)phenyl and 2-iodo-4-methylphenyl.

The term "heteroaryl" refers to a substituted or unsubstituted 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heteroaryls include, but are not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzofuranyl and benzothiofuranyl (benzothienyl). The heterocyclic ring may be optionally substituted with up to two substituents such as, but not limited to, alkyl, halo and haloalkyl.

The term "aralkyl" is used to describe a group wherein the alkyl chain can be branched or straight chain with the aryl portion, as defined hereinbefore, forming a terminal portion of the aralkyl moiety. Examples of aralkyl groups include, but are not limited to, optionally substituted benzyl and phenethyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3 -nitrophenyl)ethyl, 2-(2,4-dichlorophenyl)ethyl, 2-(3,5-dimethoxyphenyl)ethyl, 4-(trifluoromethoxy)benzyl and the like.

The term "heteroaralkyl" is used to describe a group wherein the alkyl chain can be branched or straight chain with the heteroaryl portion, as defined hereinbefore, forming a terminal portion of the heteroaralkyl moiety, for example 3-furylmethyl, thenyl (thienylmethyl), furfuryl and the like.

The compounds of formula (I) also embrace the tautomeric forms of the invention, for example

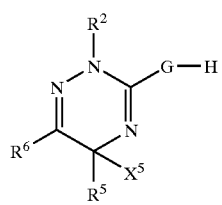

wherein $R^2$, $R^5$, $X^5$, $R^6$ and G are as previously defined.

A preferred mode of this first embodiment are compounds of formula (I) wherein
$R^2$ is $(C_1–C_{12})$alkyl, halo$(C_1–C_4)$alkyl, cyano, $(C_2–C_8)$alkenyl, $(C_2–C_8)$alkynyl, halo$(C_2–C_8)$alkynyl, cyclo$(C_3–C_7)$ alkyl$(C_2–C_8)$alkynyl, $(C_1–C_4)$alkoxy$(C_1–C_4)$alkyl, cyclo $(C3–C_7)$alkyl, cyclo$(C_3–C_7)$alkyl$(C_1–C_6)$alkyl, tri $(C_1–C_8)$alkylsilyl$(C_1–C_4)$alkyl where the three alkyl groups may be the same or different, $(C_1–C_8)$alkoxycarbonyl, $(C_1–C_8)$alkylcarbonyl, phenyl or phenyl substituted with from one to three substituents independently selected from the group consisting of $(C_1–C_4)$alkyl, halo, $(C_1–C_4)$alkoxy, halo$(C_1–C_4)$alkyl and halo$(C_1–C_4)$ alkoxy, phen$(C_1–C_4)$alkyl phenthio$(C_1–C_4)$alkyl, or phen $(C_1–C_4)$alkyl, phenthio$(C_1–C_4)$alkyl substituted on the phenyl ring with from one to three substituents independently selected from the group consisting of $(C_1–C_4)$ alkyl, halo, $(C_1–C_4)$alkoxy, halo$(C_1–C_4)$alkyl and halo $(C_1–C_4)$alkoxy, furyl, thienyl, benzothienyl or benzofuranyl,
$R^4$ is a hydrogen atom, $(C_1–C_4)$alkyl, halo$(C_1–C_4)$alkyl, cyclo$(C_3–C_8)$alkyl, cyclo$(C_3–C_8)$alkyl$(C_1–C_4)$alkyl, $(C_1–C_4)$alkylsulfonyl, $(C_2–C_8)$alkynyl, halo$(C_1–C_4)$ alkoxycarbonyl, $(C_1–C_4)$alkoxycarbonylthio, $((C_1–C_4)$ alkylthio)carbonyl, $(C_1–C_4)$alkylthiothiocarbonyl, $(C_2–C_8)$alkenyloxycarbonyl, $(C_2–C_8)$alkenylthiothiocarbonyl, $(C_2–C_8)$alkynyloxycarbonyl, $(C_2–C_8)$alkynylthiothiocarbonyl, $(C_1–C_4)$alkoxyoxalyl, $(C_1–C_4)$alkylcarbonyloxy$(C_1–C_4)$alkoxycarbonyl, phenoxythiocarbonyl, phenylthiothiocarbonyl, phenylsulfonyl, or phenoxythiocarbonyl, phenylthiothiocarbonyl, phenylsulfonyl, substituted on the phenyl ring with from one to two substituents independently selected from halo and $(C_1–C_4)$alkyl,
$R^5$ is a hydrogen atom, $(C_1–C_4)$alkoxy, $(C_1–C_4)$alkylthio, hydroxy, mercapto, cyano, phenyl or phenyl substituted on the phenyl ring with from one to three substituents independently selected from the group consisting of $(C_1–C_4)$alkyl, halo, $(C_1–C_4)$alkoxy, halo$(C_1–C_4)$alkyl and halo$(C_1–C_4)$alkoxy, when $X^5$ is a hydrogen atom or
$R^6$ is phenyl, naphthyl, or phenyl or naphthyl substituted with from one to three substituents independently selected from the group consisting of halo, $(C_1–C_4)$alkyl, halo $(C_1–C_4)$alkyl, halo$(C_1–C_4)$alkoxy, $(C_1–C_4)$alkylthio, halo $(C_1–C_4)$alkylthio, $(c_1–C_4)$alkylsulfinyl, $(C_1–C_4)$alkylsulfonyl, nitro, cyano, di$(C_1–C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently selected from halo, $(C_1–C_4)$ alkyl, $(C_1–C_4)$alkoxy, halo$(C_1–C_4)$alkoxy, halo$(C_1–C_4)$ alkyl, $(C_1–C_4)$alkylthio, nitro and cyano,
G is an oxygen atom or a sulfur atom, and
$X^5$ is a hydrogen atom.

A more preferred mode of this embodiment are compounds of formula (I) wherein
$R^2$ is $(C_1–C_{10})$alkyl, halo$(C_1–C_4)$alkyl or $(C_2–C_6)$alkynyl,
$R^4$ is a hydrogen atom or $(C_1–C_4)$alkylsulfonyl,
$R^5$ is a hydrogen atom, $(C_1–C_4)$alkoxy or $(C_1–C_4)$alkylthio,
$R^6$ is phenyl or phenyl substituted with from one to three substituents independently selected from the group consisting of halo, $(C_1–C_4)$alkyl, $(C_1–C_2)$alkoxy, halo $(C_1–C_2)$alkyl and halo$(C_1–C_2)$alkoxy, and
G is an oxygen atom.

A second embodiment of this invention relates to a fungicidal composition comprising a fungicidally effective amount of a compound of the formula (IA)

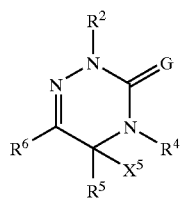

(IA)

wherein $R^2$ is alkyl, haloalkyl, cyano, alkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl or phenalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, or furyl or thienyl substituted with halo or alkyl on the furyl or thienyl ring, benzothienyl, benzofuranyl or benzothienyl or benzofuranyl substituted with halo, alkyl or haloalkyl, $R^4$ is a hydrogen atom, alkyl, haloalkyl, cycloalkyl, cycloalkylalkyl, alkylsulfonyl, cyano, alkynyl, haloalkynyl, haloalkoxycarbonyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl, aryloxythiocarbonyl, arylthiothiocarbonyl arylsulfonyl, or aryloxythiocarbonyl, arylthiothiocarbonyl, arylsulfonyl, substituted on an aromatic ring with from one to two substituents independently selected from halo and alkyl, $R^5$ is a hydrogen atom, alkoxy, alkylthio, hydroxy, mercapto, cyano, amino, alkylamino, dialkylamino wherein the alkyl groups may be the same or different or together with the nitrogen to which they are attached form a 5- or 6-membered heterocyclic ring, phenyl, phenyloxy or phenylthio or phenyl, phenoxy or phenylthio substituted on the phenyl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring, alkylcarbonyloxy, alkylcarbonylthio, alkoxycarbonyloxy, alkoxycarbonylthio, arylcarbonyloxy and arylcarbonylthio, $R^6$ is phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, thienyl, quinolinyl, isoquinolinyl, benzofuranyl, benzothienyl, pyridyl, pyridazinyl, pyrimidinyl, and furyl, thienyl, pyridyl, pyridazinyl, pyrimidinyl, substituted with one or two substituents independently selected from halo, alkyl, alkoxy, haloalkoxy, haloalkyl, alkylthio, haloalkylthio, nitro and cyano, $X^5$ is a hydrogen atom, G is an oxygen atom, a sulfur atom or the agronomically acceptable salts, isomers, tautomers, enantiomers and mixtures thereof, and an agronomically acceptable carrier.

A preferred mode of this second embodiment are fungicidal compositions of comprising a compound of formula (IA) wherein $R^2$ is $(C_1-C_{12})$alkyl, halo$(C_1-C_4)$alkyl, cyano, $(C_2-C_8)$alkenyl, $(C_2-C_8)$alkynyl, halo$(C_2-C_8)$alkynyl, cyclo$(C_3-C_7)$alkyl$(C_2-C_8)$alkynyl, $(C_1-C_4)$alkoxy$(C_1-C_4)$alkyl, cyclo$(C_3-C_7)$alkyl, cyclo$(C_3-C_7)$alkyl$(C_1-C_6)$alkyl, tri$(C_1-C_8)$alkylsilyl$(C_1-C_4)$alkyl where the three alkyl groups may be the same or different, $(C_1-C_8)$alkoxycarbonyl, $(C_1-C_8)$alkylcarbonyl, phenyl or phenyl substituted with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phen$(C_1-C_4)$alkyl or phen$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^4$ is a hydrogen atom, $(C_1-C_4)$alkyl, halo$(C_1-C_4)$alkyl, cyclo$(C_3-C_8)$alkyl, cyclo$(C_3-C_8)$alkyl$(C_1-C_4)$alkyl, $(C_1-C_4)$alkylsulfonyl, $(C_2-C_8)$alkynyl, halo$(C_1-C_4)$alkoxycarbonyl, $(C_1-C_4)$alkoxycarbonylthio, $((C_1-C_4)$alkylthio)carbonyl, $(C_1-C_4)$alkylthiothiocarbonyl, $(C_2-C_8)$alkenyloxycarbonyl, $(C_2-C_8)$alkenylthiothiocarbonyl, $(C_2-C_8)$alkynyloxycarbonyl, $(C_2-C_8)$alkynylthiocarbonyl, $(C_1-C_4)$alkoxyoxalyl, $(C_1-C_4)$alkylcarbonyloxy$(C_1-C_4)$alkoxycarbonyl, phenoxythiocarbonyl, phenylthiothiocarbonyl, phenylsulfonyl, or phenoxythiocarbonyl, phenylthiothiocarbonyl, phenylsulfonyl, substituted on the phenyl ring with from one to two substituents independently selected from halo and $(C_1-C_4)$alkyl, $R^5$ is a hydrogen atom, $(C_1-C_4)$alkoxy, $(C_1-C_4)$alkylthio, hydroxy, mercapto, cyano, alkylcarbonyloxy, alkylcarbonylthio, alkoxycarbonyloxy, alkoxycarbonylthio, phenyl, phenoxy, phenylthio, phenylcarbonyloxy, phenylcarbonylthio, or phenyl, phenoxy, phenylthio, phenylcarbonyloxy, phenylcarbonylthio substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, $R^6$ is benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl, naphthyl, or phenyl or naphthyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylthio, halo$(C_1-C_4)$alkylthio, $(C_1-C_4)$alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently selected from halo, $(C_1-C_4)$alkyl, $(C_1-C_4)$alkoxy, halo $(C_1-C_4)$alkoxy, halo$(C_1-C_4)$alkyl, $(C_1-C_4)$alkylthio, nitro and cyano, G is an oxygen atom or a sulfur atom, and $X^5$ is a hydrogen atom.

A more preferred mode of this second embodiment are fungicidal compositions comprising a compound of formula (IA) wherein $R^2$ is $(C_1-C_{10})$alkyl, halo$(C_1-C_4)$alkyl, $(C_2-C_6)$alkynyl, $R^4$ is a hydrogen atom or $(C_1-C_4)$alkylsulfonyl, $R^5$ is a hydrogen atom, $(C_1-C_4)$alkoxy or $(C_1-C_4)$alkylthio, $R^6$ is phenyl, or phenyl substituted with from one to three substituents independently selected from the group consisting of halo, $(C_1-C_4)$alkyl, $(C_1-C_2)$alkoxy, halo $(C_1-C_2)$alkyl and halo$(C_1-C_2)$alkoxy, and G is an oxygen atom.

A third embodiment of this invention relates to an insecticidal composition comprising a insecticidally effective amount of a compound of the formula (IB)

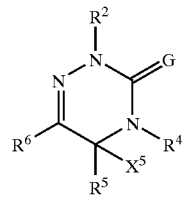

(IB)

wherein $R^2$ is alkyl, haloalkyl, cyano, cyanoalkyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl, phenylthioalkyl, or phenalkyl or phenylthioalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, thenyl or furyl, thienyl or thenyl substituted with halo or alkyl on the furyl or thienyl ring, benzothienyl, benzofuranyl or benzothienyl or benzofuranyl substituted with halo, alkyl or haloalkyl, $R^4$ is a hydrogen atom, alkyl, haloalkyl, cycloalkyl, cycloalkylalkyl, alkylsulfonyl, cyano, alkynyl, haloalkynyl, haloalkoxycarbonyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl, aryloxythiocarbonyl, arylthiothiocarbonyl or aryloxythiocarbonyl, arylthiothiocarbonyl substituted on an aromatic ring with from one to two substituents independently selected from halo and alkyl, $R^5$ is a hydrogen atom, alkoxy, alkylthio, hydroxy, mercapto, alkynyl, cyano, amino, alkylamino, dialkylamino wherein the alkyl groups may be the same or different or together with the nitrogen to which they are attached form a 5- or 6-membered heterocyclic ring, alkylcarbonyloxy, alkylcarbonylthio, alkoxycarbonyloxy or alkoxycarbonylthio, $R^6$ is phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, thienyl, quinolinyl, isoquinolinyl, benzofuranyl, benzothienyl, pyridyl, pyridazinyl, pyrimidinyl, and furyl, thienyl, pyridyl, pyridazinyl, pyrimidinyl, substituted with one or two substituents independently selected from halo, alkyl, alkoxy, haloalkoxy, haloalkyl, alkylthio, haloalkylthio, nitro and cyano, $X^5$ is a hydrogen atom or taken together with $R^4$ forms a nitrogen-carbon bond, G is an oxygen atom or a sulfur atom, or the agronomically acceptable salts, isomers, tautomers, enantiomers and mixtures thereof, and an agronomically acceptable carrier, provided that: when $R^2$ is a phenalkyl, thenyl or substituted phenalkyl or thenyl and $X^5$ is a hydrogen atom, $R^4$ is not cyano, alkylsulfonyl or polyhaloalkyl.

A preferred mode of this third embodiment are insecticidal compositions of comprising a compound of formula (IB) wherein $R^2$ is $(C_1-C_{12})$alkyl, halo$(C_1-C_4)$alkyl, cyano, cyano $(C_1-C_4)$alkyl, $(C_2-C_8)$alkynyl, halo$(C_2-C_8)$alkynyl, cyclo$(C_3-C_7)$alkyl$(C_2-C_8)$alkynyl, $(C_1-C_4)$alkoxy $(C_1-C_4)$alkyl, cyclo$(C_3-C_7)$alkyl, cyclo$(C_3-C_7)$alkyl $(C_1-C_6)$alkyl, tri$(C_1-C_8)$alkylsilyl$(C_1-C_4)$alkyl where the three alkyl groups may be the same or different, $(C_1-C_8)$ alkoxycarbonyl, $(C_1-C_8)$alkylcarbonyl, phenyl or phenyl substituted with from one to three substituents independently selected from the group consisting of $(C_1-C_4)$ alkyl, halo, $(C_1-C_4)$alkoxy, halo$(C_1-C_4)$alkyl and halo $(C_1-C_4)$alkoxy, phen$(C_1-C_4)$alkyl, phenthio$(C_1-C_4)$alkyl or phen$(C_1-C_4)$alkyl, phenthio$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^4$ is a hydrogen atom, $(C_1-C_4)$alkyl, halo$(C_1-C_4)$alkyl, cyclo$(C_3-C_8)$alkyl, cyclo$(C_3-C_8$alkyl, cyclo$(C_3-C_8)$alkyl $(C_1-C_4)$alkyl, $(C_1-C_4)$alkylsulfonyl, $(C_2-C_8)$alkynyl, halo$(C_1-C_4)$alkoxycarbonyl, $(C_1-C_4)$alkoxycarbonylthio, $((C_1-C_4)$alkylthio)carbonyl, $(C_1-C_4)$alkylthiothiocarbonyl, $(C_2-C_8)$alkenyloxycarbonyl, $(C_2-C_8)$alkenylthiothiocarbonyl, $(C_2-C_8)$alkynyloxycarbonyl, $(C_2-C_8)$alkynylthiothiocarbonyl, $(C_1-C_4)$alkoxyoxalyl, $(C_1-C_4)$ alkylcarbonyloxy$(C_1-C_4)$alkoxycarbonyl, phenoxythiocarbonyl, phenylthiothiocarbonyl or phenoxythiocarbonyl, phenylthiothiocarbonyl substituted on the phenyl ring with from one to two substituents independently selected from halo and $(C_1-C_4)$alkyl, $R^5$ is a hydrogen atom, $(C_1-C_4)$alkoxy, $(C_1-C_4)$alkylthio, hydroxy, mercapto or cyano, $R^6$ is benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl, naphthyl, or phenyl or naphthyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylthio, halo$(C_1-C_4)$alkylthio, $(C_1-C_4)$alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl fungicidally effective amount of a fungicidal composition comprising a compound of formula (IA) to the fungus, to the locus of the fungus or to the growth medium of said fungus.

A fifth embodiment of the present invention relates to a method of controlling an insect comprising applying an insecticidally effective amount of a composition comprising a compound of formula (IB) to the insect, to the locus of the insect or to the growth medium of said insect.

The compounds of this invention can be made by the methods illustrated. An α-halo ketone is reacted with the sodium salt of 2,4-thiazolidinedione to give Intermediate I. This intermediate is reacted with hydrazine or a substituted hydrazine to give a dihydrotriazinone. The dihydrotriazinones are oxidized to the triazinones by the methods shown. Other oxidants, such as tert-butylhypochlorite, may be used. When $R^2$ is hydrogen, the compounds may be reacted with an electrophile to give a derivatized triazinone.

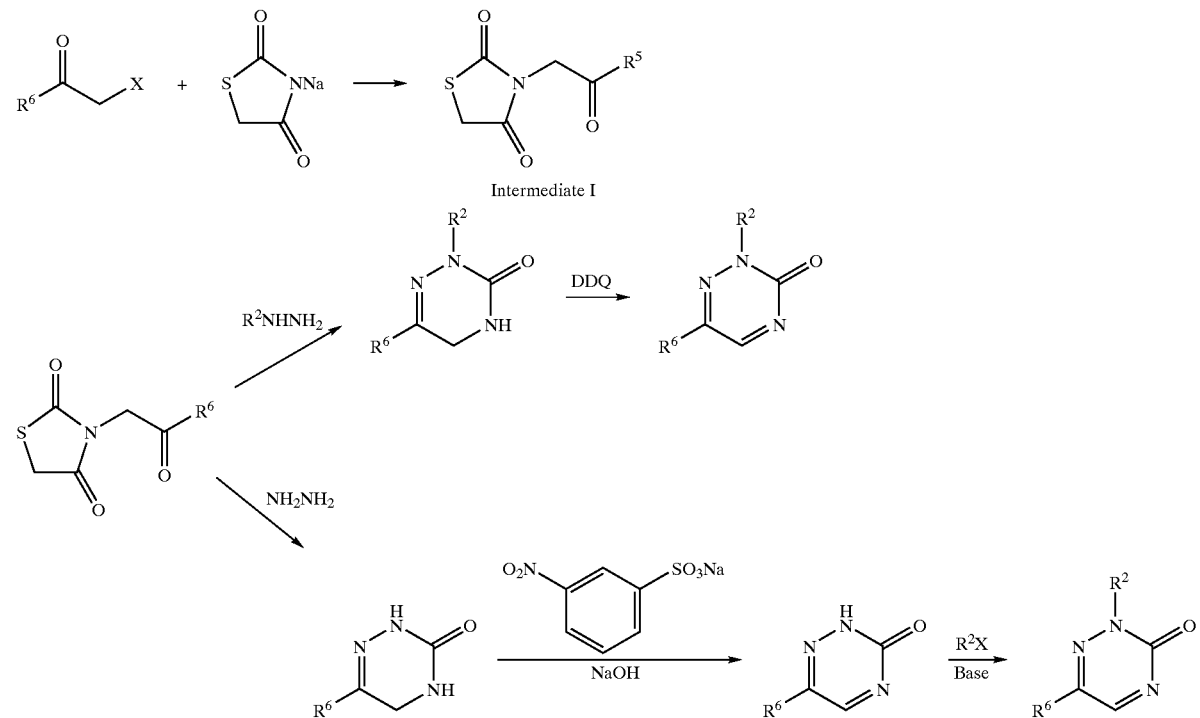

substituted with one or two substituents independently selected from halo, $(C_1-C_4)$alkyl, $(C_1-C_4)$alkoxy, halo $(C_1-C_4)$alkoxy, halo$(C_1-C_4)$alkyl, $(C_1-C_4)$alkylthio, nitro and cyano, G is an oxygen atom or a sulfur atom, and $X^5$ is a hydrogen atom or taken together with $R^4$ forms a nitrogen-carbon bond.

A more preferred mode of this third embodiment are insecticidal compositions comprising a compound of formula (IB) wherein $R^2$ is $(C_1-C_{10})$alkyl, halo$(C_1-C_4)$alkyl or $(C_2-C_6)$alkynyl, $R^4$ is a hydrogen atom or $(C_1-C_4)$alkyl, $R^5$ is a hydrogen atom, $(C_1-C_4)$alkoxy or $(C_1-C_4)$alkylthio, and $R^6$ is phenyl substituted with from one to three halogen substituents.

A fourth embodiment of the present invention relates to a method of controlling a fungus comprising applying a The $R^4$ substituent may be added by reaction of a dihydrotriazinone with an electrophile as shown in the following equation.

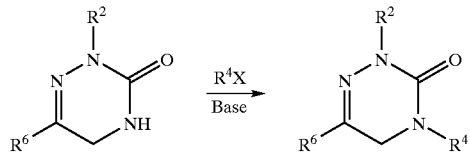

Alternatively, an N-substituted intermediate such as Intermediate II can be cyclized with a substituted or unsubstituted hydrazine to give a dihydrotriazinone.

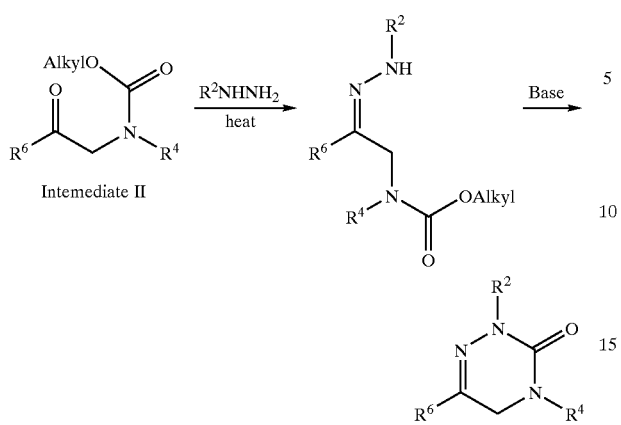

The R² substituent may be added by the reaction of a 2-unsubstituted dihydrotriazinone with an electrophile as shown in the following equation.

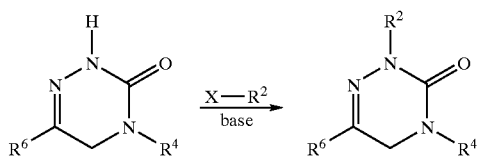

A nucleophile will react with a triazinone to introduce a substitutent at R⁵.

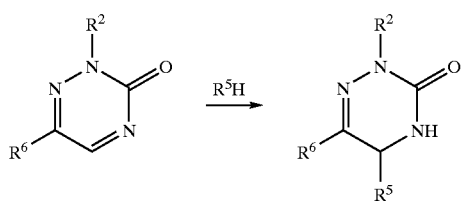

EXAMPLES DEMONSTRATING THE METHODS

All reactions were run under a blanket of nitrogen.

Preparation of 3-(2-(4-chlorophenyl)-2-oxo-ethyl)-thiazolidine-2,4-dione

To a suspension of 3.15 g of sodium hydride (60% in mineral oil, 78.8 mmol) in 70 mL of DMF at 0° C. was added 9.76 g (75 mmol) of 2,4 -thiazolidinedione portion-wise. The reaction mixture was stirred for 20 minutes, then 17.5 g of 2-bromo-4'-chloroacetophenone (75 mmol) was added. The reaction was allowed to warm to room temperature and stirred for 5 hours. Ethyl acetate and water were added, the organic phase was separated, and washed with water and brine. The combined aqueous extracts were washed with additional ethyl acetate which was then washed with water and brine and combined with the rest of the organic layer. The ethyl acetate phases were dried over magnesium sulfate, filtered and stripped to give 23 g of crude product. Recrystallization from 1:1 toluene:hexane gave 16.25 g of 3-(2-(4-chlorophenyl)-2-oxo-ethyl)-thiazolidine-2,4-dione, (85% yield) mp 122–124° C.

Preparation of 6-(4-chlorophenyl)-4,5-dihydro-1,2,4-triazin-3-one

Hydrazine hydrate (8.0 g, 160 mmol) and 19.55 g of 3-(2-(4-chlorophenyl)-2-oxo-ethyl)-thiazolidine-2,4-dione in 100 mL of methanol were stirred at room temperature over a weekend, then refluxed for 8 hours. The reaction mixture was cooled and the solids were filtered, washed with methanol and dried to give 9.06 g of white solid 6-(4-chlorophenyl)-4,5-dihydro-1,2,4-triazin-3-one (57% yield).

Preparation of 6-(4-chlorophenyl)-1,2,4-triazin-3-one

Reference to analogous procedure: Curran and Ross, J. Med. Chem. 1974 17 273.

A mixture of 3.64 g (17.4 mmol) of 6-(4-chlorophenyl)-4,5-dihydro-1,2,4-triazin-3-one, 4.0 g of sodium m-nitrobenzene sulfonate (17.8 mmol), 6.0 g of 50% sodium hydroxide (75.2 mmol) and 160 mL of water were refluxed overnight. The reaction mixture was cooled, then 1N aqueous HCl was added until the pH was slightly acidic to paper. The product was filtered, washed with water and dried to give 3.0 g of 6-(4-chlorophenyl)-1,2,4-triazin-3-one, which was used without further purification.

Preparation of 2-pentyl-5-methoxy-6-(4-chlorophenyl)-4,5-dihydro-1,2,4-triazin-3-one (Compound 1) and 2-pentyl-6-(4-chlorophenyl)-1,2,4-triazin-3-one (Compound 2)

To a suspension of 0.47 g of sodium hydride (60% in mineral oil, 11.6 mmol) in DMF at room temperature was added 2.30 g (11.1 mmol) of 6-(4-chlorophenyl)-1,2,4-triazin-3-one. The reaction mixture was stirred 2.41 g (12.2 mmol) of 1-iodopentane was added. The reaction mixture was stirred overnight. Ethyl acetate and water were added. The organic phase was separated, and washed with water and brine, then dried over magnesium sulfate, filtered and stripped to give 2.07 g of crude product. This product was mixed with 10 mL of methanol, 10 mL of ethyl acetate and 7 g of silica gel in a round bottom flask, and stirred for 3 hours at room temperature. The slurry was filtered and washed with 50 mL of methanol/ethyl acetate (1/1), and the filtrate was stripped to give 1.8 g of solid. Chromatography on neutral alumina gave 0.6 g of 2-pentyl-5-methoxy-6-(4-chlorophenyl)-4,5-dihydro-1,2,4-triazin-3-one (Compound 1).

A 0.5 g sample of 2-pentyl-5-methoxy-6-(4-chlorophenyl)-4,5-dihydro-1,2,4-triazin-3-one was dissolved in toluene. The toluene was removed from the product by distillation at atmospheric pressure to give 0.28 g of 2-pentyl-6-(4-chlorophenyl)-1,2,4-triazin-3-one (Compound 2).

Preparation of 2-n-butyl-6-(4-chlorophenyl)-4,5-dihydro-1,2,4-triazin-3-one

Butylhydrazine oxalate (41 g, 230 mmol) and 40 g of 3-(2-(4 -chlorophenyl)-2-oxo-ethyl)-thiazolidine-2,4-dione (161 mmol) in 2200 mL of methanol were cooled in an ice bath and treated with 30.3 g (300 mmol) of triethylamine. The reaction mixture was stirred at room temperature for 30 minutes, then refluxed overnight. The reaction mixture was cooled and 400 mL of water was added. This mixture was extracted with ethyl acetate. The organic phase was washed twice with 10% aqueous sodium hydroxide solution, then dried and stripped. The solids obtained were recrystallized from ethyl acetate/hexane to give 9.6 g of 2-n-butyl-6-(4-chlorophenyl)-4,5-dihydro-1,2,4-triazin-3-one.

Preparation of 2-n-butyl-5-methoxy-6-(4-chlorophenyl)-4,5-dihydro-1,2,4-triazin-3-one (Compound 3) and 2-n-butyl-6-(4-chlorophenyl)-1,2,4-triazin-3-one (Compound 4)

2-n-Butyl-6-(4-chlorophenyl)-4,5-dihydro-1,2,4-triazin-3-one (2.16 g, 8.13 mmol), and DDQ (1.94 g, 8.5 mmol in 80 mL of ethyl acetate were stirred at room temperature overnight, then refluxed for 3 hours. The reaction mixture was cooled, washed twice with aqueous potassium carbonate solution, washed with brine, dried over magnesium sulfate and stripped. The product was dissolved in 15 mL of ethyl acetate and 15 mL of methanol. Alumina (7 g) was added, and the slurry was stirred for 3 hours at room temperature. The slurry was filtered, and the filtrate was stripped. The product was chromatographed on an alumina column to give 0.97 g of of 2-n-butyl-5-methoxy-6-(4-chlorophenyl)-4,5-dihydro-1,2,4-triazin-3-one (Compound 3).

Elimination of methanol from compound 3 provided 2-n-butyl-6-(4-chlorophenyl)-1,2,4-triazin-3-one (Compound 4).

Preparation of 2-n-butyl-4-methanesulfonyl-6-(4-chlorophenyl)-4,5-dihydro-1,2,4-triazin-3-one (Compound 5)

To a slurry of 0.50 g of 2-n-butyl-6-(4-chlorophenyl)-4,5-dihydro-1,2,4-triazin-3-one (1.9 mmol) in 5 mL of THF at −78° C. was added 1.15 mL of n-BuLi (1.6 M, 1.8 mmol). The reaction mixture became a solution. Methanesulfonyl chloride (0.23 g, 2 mmol) in 1 mL of THF was added. The reaction mixture was held at −78° C. for 5 minutes, then warmed to room temperature and stirred over a weekend. Water and ethyl acetate were added. The organic phase was was washed with brine, dried over magnesium sulfate, filtered and stripped to give 0.57 g of tan solids. Chromatography on silica gel gave 0.46 g of 2-n-butyl-4-methanesulfonyl-6-(4-chlorophenyl)-4,5-dihydro-1,2,4-triazin-3-one (Compound 5), a tan solid.

Preparation of 2,6-bis-(4-chlorophenyl)-4-methyl-4,5-dihydro-1,2,4-triazin-3-one (Compound 6)

a) 2-(N-methyl-N-(methoxycarbonyl)-amino)-4'-chloroacetophenone N'-(4-chlorophenyl)hydrazone To 5.09 g (21.1 mmol) of 2-(N-methyl-N-(methoxycarbonyl)-amino)-4'-chloroacetophenone, prepared according to the method of U.S. Pat. No. 5,798,311, was added 30 g of methanol, 4.31 g (24.0 mmol) of 4-chlorophenylhydrazine hydrochloride, and 4.0 g (44.9 mmol) of sodium acetate. The mixture was refluxed for three hours, concentrated in vacuo, partitioned between ethyl acetate and water, dried over anhydrous magnesium sulfate, and reconcentrated in vacuo to yield 5.9 g of the title compound, a yellow solid, mp 114–116° C.

b) 2,6-bis-(4-chlorophenyl)-4-methyl-4,5-dihydro-1,2,4-triazin-3-one 2.97 g (8.1 mmol) of 2-(N-methyl-N-(methoxycarbonyl)-amino)-4'-chloroacetophenone N'-(4-chlorophenyl)hydrazone was dissolved in 15 g of dry tetrahydrofuran. To this solution was added 1.0 g of 20% potassium tert-butoxide in tetrahydrofuran. After refluxing the resulting red solution for 10 minutes, the reaction was concentrated in vacuo and partitioned between ethyl acetate and aqueous sodium bicarbonate. After drying the organic layer with anhydrous magnesium sulfate, filtering and concentrating in vacuo, there was obtained Compound 6 as a white solid, mp174–176° C.

Preparation of 2-propargyl-6-(4-chlorophenyl)-4-methyl-4,5-dihydro-1,2,4-triazin-3-one (Compound 7)

a) 2-(N-methyl-N-(methoxycarbonyl)-amino)-4'-chloroacetophenone hydrazone 101 g (418 mmol) of 2-(N-methyl-N-(methoxycarbonyl)-amino)-4'-chloroacetophenone was dissolved in 600 ml of warm 1-propanol. To this mixture was added 4.85 g (80 mmol) of acetic acid and 60.9 g (1218 mmol) of hydrazine monohydrate. The mixture was refluxed for two hours and then concentrated in vacuo. The residue was dissolved in ethyl acetate and washed with water and saturated aqueous sodium chloride. After drying over magnesium sulfate, filtering, and reconcentrating in vacuo, there was obtained 75.6 g of the title compound, an oil.

b) 6-(4-chlorophenyl)-4-methyl-4,5-dihydro-1,2,4-triazin-3-one 68.24 g (267 mmol) of 2-(N-methyl-N-(methoxycarbonyl)-amino)-4'-chloroacetophenone hydrazone was dissolved in 400 ml of tetrahydrofuran. To this solution was added 30 ml of 20% potassium tert-butoxide in tetrahydrofuran. The resulting reaction mixture was refluxed for two hours, concentrated in vacuo, slurried in 500 ml of 50/50 diethyl ether/hexanes and filtered. The golden solid was washed with water and dried yielding 30 g of the title compound, mp 195–197° C.

c) 2-propargyl-6-(4-chlorophenyl)-4-methyl-4,5-dihydro-1,2,4-triazin-3-one 0.46 g (11.5 mmol) of 60% sodium hydride was washed with hexane to remove oil and then suspended in 4 ml of dimethyl formamide. To this slurry was added 2.16 g (9.65 mmol) of 2-(4-chlorophenyl)-4-methyl-4,5-dihydro-1,2,4-triazin-3-one dissolved in 6 ml of dimethyl formamide. Hydrogen gas was evolved. After stirring for 15 minutes, 1.25 ml of propargyl bromide was added. After 30 minutes at room temperature, the mixture was diluted with ethyl acetate and twice washed with water. The organic layer was dried and concentrated in vacuo yielding 2.31 g of solid Compound 7, mp 159–160° C.

Preparation of 2-n-pentyl-5,6-bis-(4-methoxyphenyl)-1,2,4-triazin-3-one (Compound 8)

a) 5,6-bis-(4-methoxyphenyl)-1,2,4-triazin-3-thione

A mixture of 4,4'-dimethoxybenzil (13.6 g, 50 mmol) and 6.06 g of thiosemicarbazide (66.5 mmol) in 50 mL of glacial acetic acid were stirred at room temperature then refluxed overnight. The cooled reaction mixture was diluted with 150 mL of water and filtered. The solids were washed with water and dried. The crude product was heated with 55 mL of ethyl acetate, cooled, filtered and dried to give 10.1 g of 5,6-bis-(4-methoxyphenyl)-1,2,4-triazin-3-thione, mp 228–232° C.

b) 5,6-bis-(4-methoxyphenyl)-1,2,4-triazin-3-one

A slurry of 9.6 g of 5,6-bis-(4-methoxyphenyl)-1,2,4-triazin-3-thione (29.5 mmol) in 100 mL of water was treated with 2.64 g of 50% aqueous sodium hydroxide (33 mmol). Most of the solids dissolved. The reaction mixture was cooled in an ice bath and 3.8 g of 30% hydrogen peroxide (33 mmol) was added slowly. An additional 4 mL of hydrogen peroxide solution was added, and the reaction mixture was stirred overnight at room temperature. The solids were filtered, washed with water, and dried under vacuum to give 8.6 g of product, mp 238–242° C.

c) 2-n-pentyl-5,6-bis-(4-methoxyphenyl)-1,2,4-triazin-3-one

A mixture of 5,6-bis-(4-methoxyphenyl)-1,2,4-triazin-3-one (2.14 g, 6.9 mmol), freshly ground potassium carbonate (1.45 g, 10.5 mmol), 1.43 g of iodopentane (7.2 mmol) and 11 mL of DMF were stirred at room temperature for 6 hours. The reaction mixture was diluted with water and extracted twice with ethyl acetate. The organic phase was washed with water and brine, dried over magnesium sulfate and stripped. Column chromatography gave 0.4 g of Compound 8.

In similar manner, the following compounds were made:

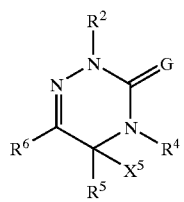

(I)

| # | $R^2$ | $R^4$ | $R^5$ | $R^6$ | $R^4$–$R^5$ forms C—N bond? |
|---|---|---|---|---|---|
| 9 | n-pentyl | hydrogen | methoxy | phenyl | no |
| 10 | n-pentyl | none | hydrogen | phenyl | yes |
| 11 | methyl | none | hydrogen | 4-chlorophenyl | yes |
| 12 | methyl | hydrogen | methoxy- | 4-chlorophenyl | no |
| 13 | tert-butyl | none | hydrogen | 4-chlorophenyl | yes |
| 14 | tert-butyl | hydrogen | methoxy | 4-chlorophenyl | no |
| 15 | phenyl | hydrogen | hydrogen | 4-chlorophenyl | no |
| 16 | phenyl | methanesulfonyl | hydrogen | 4-chlorophenyl | no |
| 17 | n-decyl | hydrogen | methoxy | 4-chlorophenyl | no |
| 18 | phenyl | hydrogen | methoxy | 4-chlorophenyl | no |
| 19 | 2,2,2-trifluoroethyl | hydrogen | hydrogen | 4-chlorophenyl | no |
| 20 | 2,2,2-trifluoromethyl | hydrogen | methoxy | 4-chlorophenyl | no |
| 21 | 2-pentynyl | methyl | hydrogen | 4-chlorophenyl | no |
| 22 | methyl | methyl | hydrogen | 4-chlorophenyl | no |
| 23 | benzyl | methyl | hydrogen | 4-chlorophenyl | no |
| 24 | cyanomethyl | methyl | hydrogen | 4-chlorophenyl | no |
| 25 | n-propyl | methyl | hydrogen | 3-chlorophenyl | no |
| 26 | phenylthiomethyl | methyl | hydrogen | 4-chlorophenyl | no |
| 27 | cyano | methyl | hydrogen | 4-chlorophenyl | no |
| 28 | propargyl | propyl | hydrogen | 4-chlorophenyl | no |
| 29 | 4-chlorobenzyl | methyl | hydrogen | 2-chlorophenyl | no |
| 30 | 4-chlorobenzyl | methyl | hydrogen | 4-chlorophenyl | no |
| 31 | 2-pentynyl | none | hydrogen | 4-chlorophenyl | yes |
| 32 | methyl | 2-pentynyl | hydrogen | 4-chlorophenyl | no |
| 33 | methyl | hydrogen | hydrogen | 4-chlorophenyl | no |
| 34 | n-pentyl | none | hydrogen | 4-methoxyphenyl | yes |

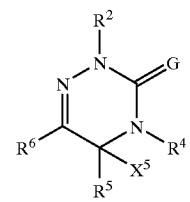

TABLE 2

Characterization of Compounds

| # | M.P. ° C. | 300 MHZ NMR |
|---|---|---|
| 1 | | (CDCl$_3$): 0.90, (t, 3H), 1.34 (m, 4H), 1.75 (pentet, 2H), 3.26, (s, 3H), 3.80 (m, 2H), 5.66 (d, 1H), 6.65 (bs, 1H), 7.37, (d, 2H), 7.73 (d, 2H) |
| 2 | | (CDCl$_3$): 0.92, (t, 3H), 1.38 (m, 4H), 1.89 (pentet, 2H), 4.22 (t, 2H), 7.49, (d, 2H), 7.74 (d, 2H), 9.03, (s, 1H) |
| 3 | | (Benzene-d6): 0.77 (t, 3H), 1.21, (m, 2H), 1.62 (m, 2H), 2.88 (s, 3H), 3.76 (m, 1H), 3.91 (m, 1H), 4.92 (d, 1H), 7.04 (2H), 7.43 (d, 2H), 7.91 (bd, 1H) |
| 4 | | (CDCl$_3$): 0.99, (t, 3H), 1.44 (hextet, 2H), 1.88 (pentet, 2H), 4.23 (t, 2H), 7.49, (d, 2H), 7.75 (d, 2H), 9.03, (s, 1H) |
| 5 | | (CDCl$_3$): 0.96, (t, 3H), 1.40 (hextet, 2H), 1.75 (pentet, 2H), 3.47 (s, 3H), 3.85 (t, 2H), 4.75 (s, 2H), 7.41, (d, 2H), 7.65 (d, 2H) |
| 6 | 174–176 | |
| 7 | 159–160 | |
| 8 | | (methanol-d4): 0.94 (t, 3H), 1.35–1.5 (m, 4H), 1.9 (quintet, 2H), 3.83 (s, 3H), 3.84 (s, 3H), 4.2 (t, 2H), 6.85 (d, 2H), 6.90 (d, 2H), 7.27 (d, 2H), 7.49 (d, 2H) |
| 9 | | (CDCl$_3$): 0.90 (t, 3H), 1.36 (m, 5H), 1.75 (pentet, 2H), 3.29 (s, 3H), 3.83 (m, 2H), 5.65 (d, 1H), 7.45 (m, 3H), 7.72 (m, 2H) |
| 10 | | (CDCl$_3$): 0.69 (t, 3H), 1.18 (m, 4H), 1.71 (m, 2H), 4.00 (t, 2H), 7.27 (m, 3H), 7.58 (m, 2H), 8.84 (s, 1H) |
| 11 | | (CDCl$_3$): 3.91 (s, 3H), 7.49 (d, 2H), 7.74 (d, 2H), 9.05 (s, 1H) |
| 12 | | (CDCl$_3$): 3.31 (s, 3H), 3.48 (s, 3H), 5.55 (d, 1H), 7.36 (d, 2H), 7.69 (m, 2H), 8.33 (bs, 1H) |
| 13 | | (CDCl$_3$): 1.73 (s), 7.5 (d), 7.75 (d), 8.95 (s) |
| 14 | | (CDCl$_3$): 1.58 (s), 3.27 (s), 5.53 (d), 7.4(d), 7.7 (d) |
| 15 | | (CDCl$_3$): 4.51 (d, 2H), 6.13 (bs, 1H), 7.28 (m, 1H), 7.42 (m, 4H), 7.58 (m, 4H) |
| 16 | | (CDCl$_3$): 3.51 (s, 3H), 4.92 (s, 2H), 7.3 (t, 1H), 7.45 (m, 4H), 7.6 (d, 2H), 7.7 (d, 2H) |

TABLE 2-continued

Characterization of Compounds

| # | M.P. ° C. | 300 MHZ NMR |
|---|---|---|
| 17 | | (ACETONE-D6): 0.9 (T, 3H), 1.3 (M, 14H), 1.7 (PENTET, 2H), 3.31 (S, 3H), 3.8 (M, 2H), 5.7 (D, 2H), 7.4 (D, 2H), 7.8 (D, 2H) |
| 18 | | (CDCl$_3$): 3.35 (s, 3H), 5.65 (d, 1H), 7.1–7.5 (m, 5H), 7.6 (d, 2H), 7.7 (d, 2H), 7.85 (bs, 1H) |
| 19 | | (DMSO-d6): 4.40 (d, 2H), 4.47 (q, 2H), 7.51 (d, 2H), 7.71 (d, 2H) |
| 20 | | (DMSO-d6): 3.24 (s, 3H), 4.4 (m, 1H), 4.8 (m, 1H), 7.6 (d, 2H), 7.8 (d, 2H), 9.2 (bs, 1H) |
| 21 | 93–98 | |
| 22 | 120–123 | |
| 23 | 104–106 | |
| 24 | 180–181 | |
| 25 | | (CDCl$_3$): 0.95 (t, 3H), 1.72 (sextet, 2H), 3.02 (s, 3H), 3.77 (t, 2H), 7.3–7.4 (m, 2H), 7.4–7.55 (m, 1H), 765 (bs, 1H) |
| 26 | 109–112 | |
| 27 | 207.5–209.5 | |
| 28 | | (CDCl$_3$): 0.98 (t, 3H), 1.67 (sextet, 2H), 2.30 (t, 1H), 3.42 (t, 2H), 4.35 (s, 2H), 4.60 (d, 2H), 7.40 (d, 2H), 7.63 (d, 2H) |
| 29 | | (CDCl$_3$): 2.95 (s, 3H), 4.35 (s, 2H), 4.90 (s, 2H), 7.2–7.5 (m, 8H) |
| 30 | | (CDCl$_3$): 3.00 (s, 3H), 4.30 (s, 2H), 4.93 (s, 2H), 7.2–7.4 (m, 6H), 7.55 (d, 2H) |
| 31 | 92–94 | |
| 32 | | (CDCl$_3$): 1.12 (t, 3H), 2.21 (qt, 2H), 3.43 (s, 3H), 4.25 (t, 2H), 4.37 (s, 2H), 7.37 (d, 2H), 7.60 (d, 2H) |
| 33 | | (CDCl$_3$): 3.43 (s, 3H), 4.07 (d, 2H), 5.30 (bs, 1H), 7.37 (d, 2H), 7.57 (d, 2H) |
| 34 | | (CDCl$_3$): 0.92 (t, 3H), 1.38 (m, 4H), 1.9 (pentet, 2H), 3.88 (s, 3H), 4.2 (t, 2H), 7.02 (d, 2H), 7.75 (d, 2H) |

The compounds of the present invention have fungitoxic activity, particularly against phytopathogenic fungi. They are active against fungi of a number of classes including Deuteromycetes (Fungi Imperfecti), Basidiomycetes, Phycomycetes and Ascomycetes. More particularly, the method of this invention provides for activity against organisms including, but not limited to, *Pyricularia oryzae, Phytophthora infestans, Puccinia recondita, Colletotrichum lagenarium, Septoria nodorum, Plasmopara viticola, Pseudoperonospora cubensis, Uncinula necator* and *Monilinia* species.

The compounds of the invention can be applied as fungicidal sprays by methods commonly employed, such as conventional high-gallonage hydraulic sprays, low-gallonage sprays, air-blast, aerial sprays and dusts. Such use conveniently permits treatment of fungal infestations in crops such as vegetables, fruits, ornamentals, seeds, turf, cereal and vines among other plants. The dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

The compounds of the present invention are useful for the control of fungi and can be utilized at various loci such as the seed, the water surface, the soil or the foliage. For such purposes, these compounds can be used in the technical or pure form as prepared, as solutions or as formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and when desired suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in McCutcheon's Emulsifiers and Detergents, McCutcheon's Emulsifiers and Detergents and McCutcheon's Functional Materials all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds of the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates; this can be as high as 75%.

Wettable powders suitable for spraying can be prepared by admixing the compound with finely divided solid, such as inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of a compound of this invention, 45 parts of a synthetic precipitated hydrated silicon dioxide sold under the trademark Hi-Sil® and 5 parts of sodium lignosulfonate (Marasperse® N-22). In another preparation of a Kaolin type, (Barden) clay is used in place of the Hi-Sil in the above wettable powder and in another such preparation 25% of the Hi-Sil is replaced with a synthetic sodium silicoaluminate sold under the trademark Zeolex® 7.

Dusts are prepared by mixing the compounds of the invention with finely divided inert solids which can be organic or inorganic in nature. Materials useful for this purpose include botanical-flours, silicas, silicates and carbonates. One convenient method for preparing a dust is to dilute a wettable powder with a finely divided carrier. Dust concentrates containing 20% to 80% of the active ingredient are commonly made and are subsequently diluted to 1% to 10% use concentration.

The compounds of the present invention may be utilized in combination with other fungicides such as ferbam, ziram, maneb, mancozeb, zineb, propineb, metham, thiram, the complex of zineb and polyethylene thiuram disulfide, dazomet and mixtures of these with copper salts, dinocap, binapacryl, 2-sec-butyl-4,6-dinitrophenyl isopropyl carbonate, captan, folpet, glyodin, anilazine, ditalimfos, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, fenbuconazole, hexaconazole, cyproconazole, tebuconazole, epoxiconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, triforine, chlorothalonil, dichione, chloroneb, tricamba, TCPN, dichloran, 2-chloro-1-nitropropane, polychloronitrobenzenes such as pentachloronitrobenzene (PCNB), tetrafluorodichloroacetone, griseofulvin, kasugamycin, polyoxin, validamycin, streptomycin, copper hydroxide, cuprous oxide, basic cupric chloride, basic copper carbonate, copper terephthalate, copper naphthenate, Bordeaux mixture, dodine, p-dimethylaminobenzenesodium sulfonate, methyl isothiocyanate, 1-thiocyano-2,4-dinitrobenzene, 1-phenylthio-semicarbazide, calcium cyanamide, lime sulfur, thiophanate-methyl, flutolanil, edifenphos, isoprothiolane, probenazole, iprobenfos, tricyclazole, pyroquilon, dimethomorph, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin, trifloxystrobin and zoxamide.

Fungicidal Testing Protocols and Test Data

Examples of diseases against which the compounds of the invention are useful include rice diseases such as rice blast, cereal diseases such wheat leaf rust and septoria, tomato and potato late blight, grape and cucumber powdery mildew, grape and cucumber downy mildew apple scab, brown rot of fruits, and cucumber anthracnose.

Fungicide Screening for Control of Rice Blast and Cucumber Powdery Mildew

Plant Propagation:

Plants used in the fungicide testing program were grown in 2¼-inch (5.7-cm) square pots containing RediEarth propagation substrate. The plants were raised under greenhouse conditions. The rice plants were 12-days-old and cucumbers were 13-days-old at the time of spraying with chemical treatments.

Sample Preparation:

The sample of the experimental chemical was weighed and dissolved in an acetone-methanol-water solution (A/M/W at 1:1:2 ratio by volume).

Spraying Procedure:

After sprayer calibration, the test solutions were poured into the fungicide sprayer. The fungicide sprayer contains three spray nozzles, located approximately 10 cm above and to the sides of the plants. The spray produced by the nozzles results in uniform coverage of both the upper and lower parts of the plant leaves. After spraying, the treated plants were placed in a drying chamber for 4 hours, prior to sorting.

Cucumber Powdery Mildew:

Cucumber Powdery Mildew (CPM), caused by the fungus *Sphaerotheca fuliginea*, was maintained on large cucumber plants. For inoculum preparation, five to eight leaves depending on size, completely covered with powdery mildew spores, were collected. The leaves were placed in a glass jar and covered with 500 ml of water, containing 5 drops of Tween-80. The material was filtered through two layers of cheesecloth to remove leaf fragments. The spore count was adjusted to $2\times10^5$ spores per ml.

Cucumber plants, cv. "Bush Champion," were used for this test. The plants were thinned to one per pot after the cotyledons were fully developed. Two days before the test, the small leaves and meristem region were removed, leaving only the cotyledons and one large true leaf.

The protectant tests required that the cucumber plants be inoculated 1 day after spraying with the chemical treatment. The plants were inoculated with a hand-held spray bottle with the suspension of fungal spores. The leaves were lightly misted on the upper surface from two different spray directions. Disease development occurred in the greenhouse.

After seven days, the plants were evaluated for percent of disease control. The results are reported as percent control; 100 is total disease control, 0 is no disease control.

Rice Blast:

Rice Blast (RB), caused by the fungus *Pyricularia oryzae*, was maintained on potato dextrose agar (PDA) plates under fluorescent lamps at room temperature. Six different isolates of the fungus were used to prepare the inoculum. Approximately 5 plates of each isolate were used to prepare 250 ml of inoculum. The plates were flooded with water and scraped gently with a rubber spatula. The spore suspension was filtered through one layer of cheese cloth to remove mycelial fragments and agar pieces. The spore count was adjusted to achieve a concentration of $5\times10^6$ spores per ml.

Rice plants cv. "M-201," were-used for this test. The protectant tests required that the rice plants be inoculated 1 day after spraying with the chemical treatment. The curative tests in the primary screen required that the plants be inoculated 1 day after spraying with the treatment. The plants were inoculated with fungal spores using a DeVilbiss atomizer, using a spray pressure of 30 psi (200 kPa). The inoculated plants were quickly placed in a mist chamber with 100% relative humidity (RH) at 20° C. for one day and two nights; approximately 40 hours. The plants were moved to the greenhouse for disease development.

Six days after inoculation, the treatment comparisons were made. The results are reported as percent control; 100 is total disease control, 0 is no disease control.

Table 3: Protectant Fungicide Data at 300 g/ha for Rice Blast (RB) and Cucumber Powdery Mildew (CPM) in the greenhouse, given in percent control. NT means not tested.

| COMPOUND # | RB | CPM |
|---|---|---|
| 1 | 85 | 0 |
| 2 | 85 | 50 |
| 3 | 85 | 0 |
| 4 | 85 | 0 |
| 5 | 0 | 90 |
| 8 | 50 | 0 |
| 9 | 85 | 0 |
| 10 | 80 | 0 |
| 11 | 80 | 0 |
| 12 | 80 | 0 |
| 13 | 85 | 0 |
| 14 | 90 | 50 |
| 15 | 75 | 0 |
| 16 | 50 | 0 |
| 17 | 80 | 0 |
| 18 | 85 | 80 |
| 19 | 75 | 0 |
| 20 | 80 | 0 |
| 27 | 50 | 0 |
| 28 | 50 | 0 |
| 29 | 50 | NT |
| 30 | 75 | NT |
| 31 | 85 | 50 |
| 32 | 75 | 75 |
| 33 | 80 | 0 |
| 34 | 85 | 0 |

For insecticidal use, the compositions and compounds of this invention can be applied directly to the locus to be protected, as for example, the area around or upon economic plants infected with insects or to plants on which infestation is to be prevented. These compounds control injurious insects belonging to a number of orders, especially those of Lepidoptera and Homoptera. The compounds and compositions may be used either as contact or systemic pesticides. The compounds of the invention are applied to the insect's habitat at a rate of 0.0005 to 10 kilograms per hectare, preferably 0.05 to 5 and more preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habitat thereof (i.e, the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

Insecticidal Testing Protocol and Test Data

Numerous compounds of this invention were tested for insecticidal activity according to the following protocol.

1. Test Solution Preparation

A test solution containing 600 parts per million (ppm) was prepared by dissolving the appropriate weight of compound in solvent (acetone:methanol, 1:1), adding surfactant (Triton X-155 and Triton B-1956, approximately 1 oz/100 gal) and then tap water to give an acetone methanol: water system of 5:5:90. Lower concentrations of 150 and 38 ppm were made by serially diluting the 600 ppm test solution while maintaining constant solvent, water and surfactant levels.

2. Sprayers

The enclosed spraying chamber consisted of a single spray nozzle mounted on a boom moving at a fixed speed and distance over stationary targets. The vertical distance from the nozzle tip to the targets was 5.5 inches. The boom speed was 100 inches per 5 seconds. The boom passed only once over the targets.

3. Test Species
Tests were conducted with the following pests.

| Symbol | Common Name | Latin Name |
|---|---|---|
| AW | Southern Armyworm | *Spodoptera eridania* |
| TBW | Tobacco Budworm | *Heliothis virenscens* |

4. Procedure for the Foliar Species

A. Southern Armyworm
Individual fully expanded primary lima bean (*Phaseolus limensis*) leaves were placed bottom side up on moistened pieces of filter paper in Petri dishes. The leaves were sprayed with the test solutions and allowed to dry. The dishes were infested with 10 third instar larvae of the southern armyworm, covered with the lids, and held at 27° C. Armyworm control was rated by visual inspection after 96 hours. LC50 values are calculated from the data.

B. Tobacco Budworm
Individual cotton (*Gossypium hirsutum*) leaves were placed bottom side up on moistened pieces of filter paper in Petri dishes. The leaves were sprayed with the test solutions and allowed to dry. The dishes were infested with 5 neonate larvae of the tobacco budworm, covered with the lids, and held at 27° C. Percent mortality was determined 4 days post-treatment. LC50 values are calculated from the data.

TABLE 4

LC50 Insecticide data for compounds of the invention

| # | AW | TBW |
|---|---|---|
| 6 | 150 | >600 |
| 7 | 150 | 150 |
| 11 | 150 | 150 |
| 12 | 150 | 150 |
| 19 | 150 | 150 |
| 20 | 150 | 150 |
| 21 | >600 | 31 |
| 22 | 500 | 360 |
| 23 | 600 | >600 |
| 24 | 50 | >600 |
| 25 | 500 | >600 |
| 26 | 500 | >600 |
| 27 | 45 | >600 |
| 30 | 500 | 740 |

We claim:

1. A method of controlling a fungus comprising applying a fungicidal composition comprising a fungicidally effective amount of a compound of the formula

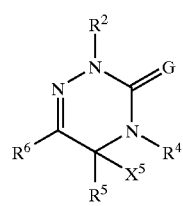

(IA)

wherein
$R^2$ is alkyl, haloalkyl, cyano, alkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl or phenalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, or furyl or thienyl substituted with halo or alkyl on the furyl or thienyl ring, benzothienyl, benzofuranyl or benzothienyl or benzofuranyl substituted with halo, alkyl or haloalkyl, $R^4$ is a hydrogen atom, alkyl, haloalkyl, cycloalkyl, cycloalkylalkyl, alkylsulfonyl, cyano, alkynyl, haloalkynyl, haloalkoxycarbonyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl, aryloxythiocarbonyl, arylthiothiocarbonyl arylsulfonyl, or aryloxythiocarbonyl, arylthiothiocarbonyl, arylsulfonyl, substituted on an aromatic ring with from one to two substituents independently selected from halo and alkyl, $R^5$ is a hydrogen atom, alkoxy, alkylthio, hydroxy, mercapto, cyano, amino, alkylamino, dialkylamino wherein the alkyl groups may be the same or different or together with the nitrogen to which they are attached form a 5- or 6-membered heterocyclic ring, phenyl, phenyloxy or phenylthio or phenyl, phenoxy or phenylthio substituted on the phenyl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring, alkylcarbonyloxy, alkylcarbonylthio, alkoxycarbonyloxy, alkoxycarbonylthio, arylcarbonyloxy and arylcarbonylthio, $R^6$ is phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, thienyl, quinolinyl, isoquinolinyl, benzofuranyl, benzothienyl, pyridyl, pyridazinyl, pyrimidinyl, and furyl, thienyl, pyridyl, pyridazinyl, pyrimidinyl, substituted with one or two substituents independently selected from halo, alkyl, alkoxy, haloalkoxy, haloalkyl, alkylthio, haloalkylthio, nitro and cyano, $X^5$ is a hydrogen atom, G is an oxygen atom, a sulfur atom or the agronomically acceptable salt, isomer, tautomer, enantiomer or mixture thereof, and an agronomically acceptable carrier, to the locus of a fungus or to the growth medium of said fungus.

2. The method of claim 1 wherein $R^2$ is $(C_1-C_{12})$alkyl, halo$(C_1-C_4)$alkyl, cyano, $(C_2-C_8)$alkenyl, $(C_2-C_8)$alkynyl, halo$(C_2-C_8)$alkynyl, cyclo$(C_3-C_7)$alkyl$(C_2-C_8)$alkynyl, $(C_1-C_4)$alkoxy$(C_1-C_4)$alkyl, cyclo$(C_3-C_7)$alkyl, cyclo$(C_3-C_7)$alkyl$(C_1-C_6)$alkyl, tri$(C_1-C_8)$alkylsilyl$(C_1-C_4)$alkyl where the three alkyl groups may be the same or different, $(C_1-C_8)$alkoxycarbonyl, $(C_1-C_8)$alkylcarbonyl, phenyl or phenyl substituted with from one to three substituents independently selected from the group consisting of$(C_1-C_4)$alkyl, halo, $(C_1-C_4)$alkoxy, halo$(C_1-C_4)$alkyl and halo$(C_1-C_4)$alkoxy, phen$(C_1-C_4)$alkyl or phen$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^4$ is a hydrogen atom, $(C_1-C_4)$alkyl, halo$(C_1-C_4)$alkyl, cyclo$(C_3-C_8)$alkyl, cyclo$(C_3-C_8)$alkyl$(C_1-C_4)$alkyl, $(C_1-C_4)$alkylsulfonyl, $(C_2-C_8)$alkynyl, halo$(C_1-C_4)$alkoxycarbonyl, $(C_1-C_4)$alkoxycarbonylthio, $(C_1-C_4)$alkylthio)carbonyl, $(C_1-C_4)$alkylthiothiocarbonyl, $(C_2-C_8)$alkenyloxycarbonyl, $(C_2-C_8)$alkenylthiothiocarbonyl, $(C_2-C_8)$alkynyloxycarbonyl, $(C_2-C_8)$alkynylthiothiocarbonyl, $(C_1-C_4)$alkoxyoxalyl, $(C_1-C_4)$alkylcarbonyloxy$(C_1-C_4)$alkoxycarbonyl, phenoxythiocarbonyl, phenylthiothiocarbonyl, phenylsulfonyl, or phenoxythiocarbonyl, phenylthiothiocarbonyl, phenylsulfonyl, substituted on the phenyl ring with from one to two substituents independently selected from halo and $(C_1-C_4)$alkyl, $R^5$ is a hydrogen atom, $(C_1-C_4)$alkoxy, $(C_1-C_4)$alkylthio, hydroxy, mercapto, cyano, alkylcarbonyloxy, alkylcarbonylthio, alkoxycarbonyloxy, alkoxycarbonylthio, phenyl, phenoxy, phenylthio, phenylcarbonyloxy, phenylcarbonylthio, or phenyl, phenoxy, phenylthio, phenylcarbonyloxy, phenylcarbonylthio substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, $R^6$ is benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl, naphthyl, or phenyl or naphthyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylthio, halo$(C_1-C_4)$alkylthio, $(C_1-C_4)$alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently selected from halo, $(C_1-C_4)$alkyl, $(C_1-C_4)$alkoxy, halo$(C_1-C_4)$alkoxy, halo$(C_1-C_4)$alkyl, $(C_1-C_4)$alkylthio, nitro and cyano, G is an oxygen atom or a sulfur atom, and $X^5$ is a hydrogen atom.

3. The method of claim 2 wherein $R^2$ is $(C_1-C_{10})$alkyl, halo$(C_1-C_4)$alkyl, $(C_2-C_6)$alkynyl, $R^4$ is a hydrogen atom or $(C_1-C_4)$alkylsulfonyl, $R^5$ is a hydrogen atom, $(C_1-C_4)$alkoxy or $(C_1-C_4)$alkylthio, $R^6$ is phenyl, or phenyl substituted with from one to three substituents independently selected from the group consisting of halo, $(C_1-C_4)$alkyl, $(C_1-C_2)$alkoxy, halo $(C_1-C_2)$alkyl and halo$(C_1-C_2)$alkoxy, and G is an oxygen atom.

4. A method of controlling an insect comprising applying an insecticidal composition comprising a insecticidally effective amount of a compound of the formula

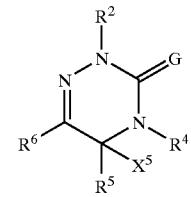

(IB)

wherein $R^2$ is alkyl, haloalkyl, cyano, cyanoalkyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl, phenylthioalkyl, or phenalkyl or phenylthioalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, or furyl or thienyl substituted with halo or alkyl on the furyl or thienyl ring, benzothienyl, benzofuranyl or benzothienyl or benzofuranyl substituted with halo, alkyl or haloalkyl, $R^4$ is a hydrogen atom, alkyl, haloalkyl, cycloalkyl, cycloalkylalkyl, alkylsulfonyl, cyano, alkynyl, haloalkynyl, haloalkoxycarbonyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl, aryloxythiocarbonyl, arylthiothiocarbonyl or aryloxythiocarbonyl, arylthiothiocarbonyl substituted on an aromatic ring with from one to two substituents independently selected from halo and alkyl, $R^5$ is a hydrogen atom, alkoxy, alkylthio, hydroxy, mercapto, alkynyl, cyano, amino, alkylamino, dialkylamino wherein the alkyl groups may be the same or different or together with the nitrogen to which they are attached form a 5- or 6-membered heterocyclic ring, alkylcarbonyloxy, alkylcarbonylthio, alkoxycarbonyloxy or alkoxycarbonylthio, $R^6$ is phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, thienyl, quinolinyl, isoquinolinyl, benzofuranyl, benzothienyl, pyridyl, pyridazinyl, pyrimidinyl, and furyl, thienyl, pyridyl, pyridazinyl, pyrimidinyl, substituted with one or two substituents independently selected from halo, alkyl, alkoxy, haloalkoxy, haloalkyl, alkylthio, haloalkylthio, nitro and cyano, $X^5$ is a hydrogen atom or taken together with $R^4$ forms a nitrogen-carbon bond, G is an oxygen atom or a sulfur atom, or the agronomically acceptable salt, isomer, tautomer, enantiomers or mixture thereof, and an agronomically acceptable carrier, provided that:

when $R^2$ is a phenalkyl, thenyl or substituted phenalkyl or thenyl and $X^5$ is a hydrogen atom, $R^4$ is not cyano, alkylsulfonyl or polyhaloalkyl, to an insect, to a locus of the insect or to a growth medium of said insect.

5. The method of claim 4 wherein $R^2$ is $(C_1–C_{12})$alkyl, halo$(C_1–C_4)$alkyl, cyano, cyano $(C_1–C_4)$alkyl, $(C_2–C_8)$alkynyl, halo$(C_2–C_8)$alkynyl, cyclo$(C_3–C_7)$alkyl$(C_2–C_8)$alkynyl, $(C_1–C_4)$alkoxy $(C_1–C_4)$alkyl, cyclo$(C_3–C_7)$alkyl, cyclo$(C_3–C_7)$alkyl $(C_1–C_6)$alkyl, tri$(C_1–C_8)$alkylsilyl$(C_1–C_4)$alkyl where the three alkyl groups may be the same or different, $(C_1–C_8)$alkoxycarbonyl, $(C_1–C_8)$alkylcarbonyl, phenyl or phenyl substituted with from one to three substituents independently selected from the group consisting of $(C_1–C_4)$alkyl, halo, $(C_1–C_4)$alkoxy, halo$(C_1–C_4)$ alkyl and halo$(C_1–C_4)$alkoxy, phen$(C_1–C_4)$alkyl, phenthio$(C_1–C_4)$alkyl or phen$(C_1–C_4)$alkyl, phenthio $(C_1–C_4)$alkyl substituted on the phenyl ring with from one to three substituents independently selected from the group consisting of $(C_1–C_4)$alkyl, halo, $(C_1–C_4)$ alkoxy, halo$(C_1–C_4)$alkyl and halo$(C_1–C_4)$alkoxy, furyl, thienyl, benzothienyl or benzofuranyl, $R^4$ is a hydrogen atom, $(C_1–C_4)$alkyl, halo$(C_1–C_4)$alkyl, cyclo$(C_3–C_8)$alkyl, cyclo$(C_3–C_8)$alkyl$(C_1–C_4)$alkyl, $(C_1–C_4)$alkylsulfonyl, $(C_2–C_8)$alkynyl, halo$(C_1–C_4)$ alkoxycarbonyl, $(C_1–C_4)$alkoxycarbonylthio, $(C_1–C_4)$ alkylthio)carbonyl, $(C_1–C_4)$alkylthiothiocarbonyl, $(C_2–C_8)$alkenyloxycarbonyl, $(C_2–C_8)$alkenylthiothiocarbonyl, $(C_2–C_8)$alkynyloxycarbonyl, $(C_2–C_8)$alkynylthiothiocarbonyl, $(C_1–C_4)$alkoxyoxalyl, $(C_1–C_4)$ alkylcarbonyloxy$(C_1–C_4)$alkoxycarbonyl, phenoxythiocarbonyl, phenylthiothiocarbonyl or phenoxythiocarbonyl, phenylthiothiocarbonyl substituted on the phenyl ring with from one to two substituents independently selected from halo and $(C_1–C_4)$alkyl, $R^5$ is a hydrogen atom, $(C_1–C_4)$alkoxy, $(C_1–C_4)$alkylthio, hydroxy, mercapto or cyano, $R^6$ is benzyl, phenethyl or benzyl or phenethyl substituted on the phenyl ring with from one to three substituents independently selected from the group consisting of $(C_1–C_4)$alkyl, halo, $(C_1–C_4)$alkoxy, halo$(C_1–C_4)$alkyl and halo$(C_1–C_4)$alkoxy, phenyl, naphthyl, or phenyl or naphthyl substituted with from one to three substituents independently selected from the group consisting of halo, $(C_1–C_4)$alkyl, halo$(C_1–C_4)$alkyl, halo$(C_1–C_4)$ alkoxy, $(C_1–C_4)$alkylthio, halo$(C_1–C_4)$alkylthio, $(C_1–C_4)$alkylsulfinyl, $(C_1–C_4)$alkylsulfonyl, nitro, cyano, di$(C_1–C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently selected from halo, $(C_1–C_4)$alkyl, $(C_1–C_4)$alkoxy, halo$(C_1–C_4)$ alkoxy, halo$(C_1–C_4)$alkyl, $(C_1–C_4)$alkylthio, nitro and cyano, G is an oxygen atom or a sulfur atom, and $X^5$ is a hydrogen atom or taken together with $R^4$ forms a nitrogen-carbon bond.

6. The method of claim 4 wherein $R^2$ is $(C_1–C_{10})$alkyl, halo$(C_1–C_4)$alkyl or $(C_2–C_6)$alkynyl, $R^4$ is a hydrogen atom or $(C_1–C_4)$alkyl, $R^5$ is a hydrogen atom, $(C_1–C_4)$alkoxy or $(C_1–C_4)$alkylthio, and $R^6$ is phenyl substituted with from one to three halogen substituents.

* * * * *